United States Patent [19]

Franke

[11] Patent Number: 4,741,008
[45] Date of Patent: Apr. 26, 1988

[54] LITHOTRIPTOR

[75] Inventor: Kurt Franke, Erlangen, Fed. Rep. of Germany

[73] Assignee: Siemens Aktiengesellschaft, Berlin and Munich, Fed. Rep. of Germany

[21] Appl. No.: 25,660

[22] Filed: Mar. 13, 1987

[30] Foreign Application Priority Data

Apr. 21, 1986 [DE] Fed. Rep. of Germany ....... 3613457

[51] Int. Cl.⁴ ..................... G01N 23/08; A61B 17/22; A61B 17/00
[52] U.S. Cl. ....................................... 378/53; 378/51; 378/99; 128/328
[58] Field of Search ............................ 378/51, 53, 99; 128/328

[56] References Cited

FOREIGN PATENT DOCUMENTS 0081051 6/1983 European Pat. Off. .
2412161 9/1974 Fed. Rep. of Germany ........ 378/53
3122056 12/1982 United Kingdom .
0211680 2/1987 United Kingdom ................ 128/328

OTHER PUBLICATIONS

Chaussy, Christian et al., *Shock Wave Treatment for Stones in the Upper Urinary Tract*, Urologic Clinics of North America, vol. 10, No. 4, Nov. 1983, pp. 743-749.

Primary Examiner—Carolyn E. Fields
Assistant Examiner—Joseph A. Hynds
Attorney, Agent, or Firm—Hill, Van Santen, Steadman & Simpson

[57] ABSTRACT

A lithotriptor station has a shockwave generator connected to a drive circuit and an x-ray system for generating an image of the calculi to be disintegrated. An output of the x-ray system is applied to a detection circuit which forms an electrical signal corresponding to the degree of calculus disintegration in the x-ray image. The electrical signal is supplied through a computer to the drive circuit for the shockwave generator for controlling the number of shockwaves administered.

7 Claims, 1 Drawing Sheet

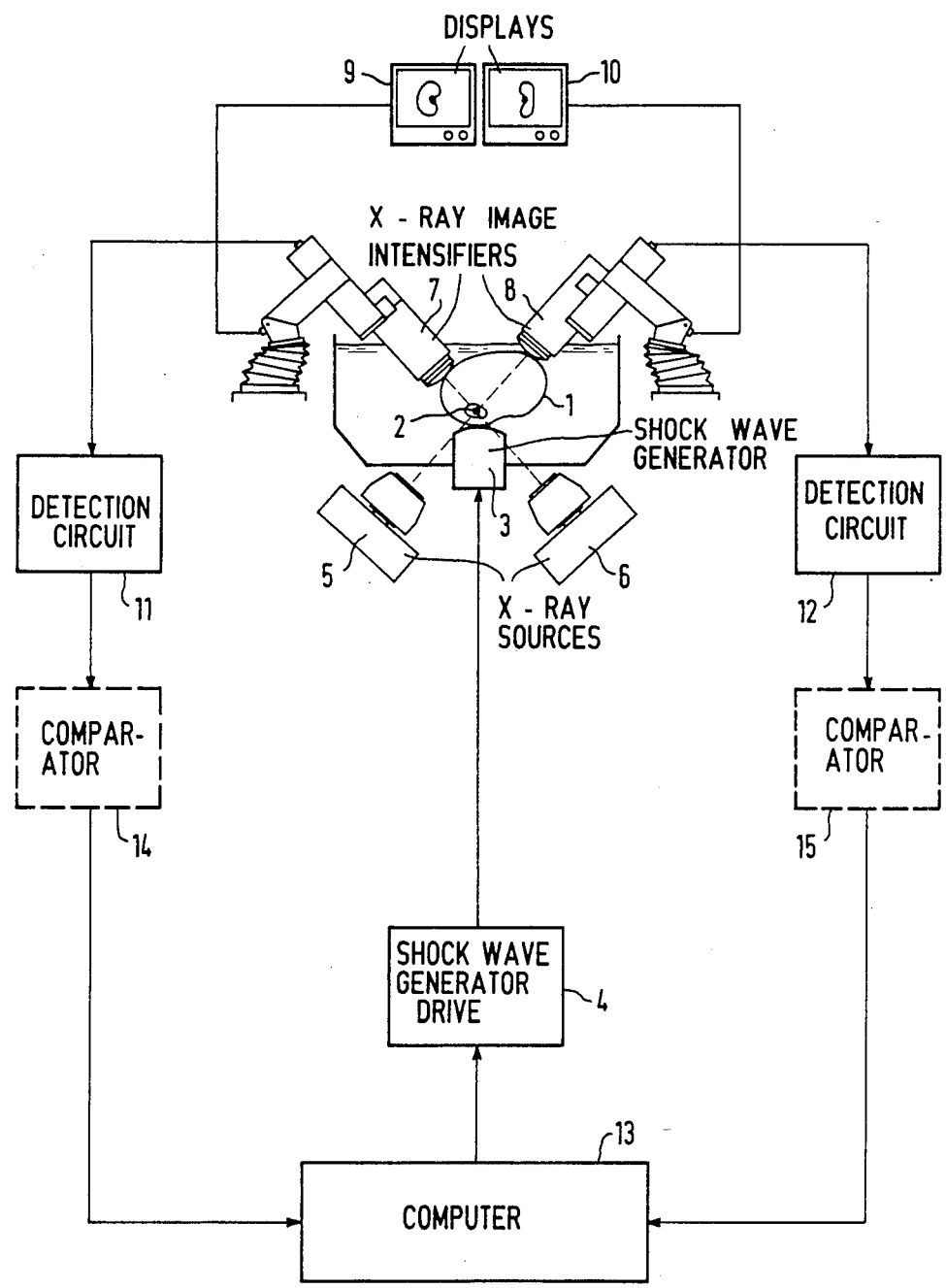

LITHOTRIPTOR

BACKGROUND OF THE INVENTION

1. Field of the Invention

The present invention relates to a lithotriptor, and in particular to a lithotriptor having a shockwave generator connected to a drive circuit an an x-ray system for representing an image of the calculi to be disintegrated.

2. Description of the Prior Art

The use of x-ray means in lithotriptor systems is known for the purpose of locating the calculi to be disintegrated. This enables the shockwave generator to be focussed exactly to the calculus to be disintegrated. In order to avoid disintegrating healthy tissue outside of the calculi, only a defined plurality of shockwaves, for example 50 shockwaves, is administered. The subsequent initiation of a new shockwave or a new series of shockwaves must be manually done by the attending physician. After a series of, for example, 50 shockwaves, a switch for initiating a further series of, for example, 50 shockwaves must be actuated. This requires special care in the treatment. It is possible, however, that the calculus will be disintegrated after only a few shockwaves following initiation of the second series of shockwaves. The remainder of the second series of shockwaves would thus not be required.

SUMMARY OF THE INVENTION

It is an object of the present invention to provide a lithotriptor wherein only the exact number of shockwaves are administered as are needed to disintegrate the calculus being treated.

The above object is achieved in accordance with the principles of the present invention by the use of a detection circuit connected to an output of the x-ray system. The detection circuit forms an electrical signal corresponding to the degree of calculus disintegration in the x-ray image associated therewith. When the decomposition of the calculus has proceeded to a prescribed value, further treatment with shockwaves is no longer required. The electrical signal formed by the detector circuit may be compared to a predetermined value, so that a lower limit of the calculus size at which treatment can be terminated can be automatically recognized. Treatment can be automatically ended by supplying the electrical signal corresponding to the size of the calculus to a computer which in turn controls operation of the drive circuit for the shockwave generator.

It is also possible to obtain an electrical signal corresponding to the size of the calculus from voltages present in the video channel of an x-ray video means.

DESCRIPTION OF THE DRAWING

The single FIGURE is a schematic block circuit diagram of a lithotriptor constructed in accordance with the principles of the present invention.

DESCRIPTION OF THE PREFERRED EMBODIMENTS

As shown in the drawing, a patient 1 having, for example, a kidney stone 2 which is to be disintegrated by lithotripsy is placed in a tub containing water. A shockwave generator 3, which generates shockwaves for disintegrating the kidney stone 2 is applied to the patient in the tub. The shockwave generator 3 is operated and supplied by a shockwave generator drive circuit 4. An x-ray system is provided for visually representing the calculi. The x-ray system may, for example, consist of two x-ray sources 5 and 6 having respective x-ray image intensifiers 7 and 8 allocated thereto. Each x-ray image intensifier 7 and 8 has an associate video chain, not shown in further detail, connected thereto. The central rays from each of the x-ray sources 5 and 6 are in a common plane and intersect at an angle of, for example, approximately 90°. The two x-ray images produced in this manner are displayed on respective monitors 9 and 10.

The video signals of the two image intensifiers 7 and 8 are supplied to two detection circuits 11 and 12 which identify the size of the calculus in the image and generate a corresponding electrical signal which is supplied to a computer 13. The computer 13 identifies the actual size of the calculus, that is, the size of the calculus fragments formed during disintegration, from the sizes of the calculi in the two x-ray images. When the actual calculus size falls below a predetermined value, the computer 13 automatically stops the shockwave generator drive circuit 4, so that no unnecessary shockwaves are adminstered to the patient.

As shown in dashed lines, it is possible to connect respective comparators 14 and 15 between the outputs of the detection circuits 11 and 12 and the computer 13. Each comparator 14 and 15 has a predetermined threshold value defined for the size of the calculus in the respective x-ray image. When the signal from the respective detection circuit connected thereto falls below this value in both channels, the shockwave generator drive circuit is shut off.

The appropriate values for causing the shockwave generator drive circuit 4 to be shut off are defined by the calculus fragments formed during disintegration reaching a size by which natural calculus elimination is possible.

Although modifications and changes may be suggested by those skilled in the art, it is the intention of the inventor to embody within the patent warranted hereon all changes and modifications as reasonably and properly come within the scope of his contribution to the art.

I claim as my invention:

1. A lithotriptor for disintegrating a calculus in a patient comprising:
   a shockwave generator for generating shockwaves for disintegrating said calculus;
   an x-ray system for generating an image of said calculus during disintegraton;
   a detection circuit connected to said x-ray system for generating a signal corresponding to the degree of disintegration of said calculus; and
   means for preventing said shockwave generator from supplying further shockwaves to said patient when said signal from said detection circuit reaches a predetermined value.

2. A lithotriptor as claimed in claim 1 wherein said x-ray system comprises two x-ray sources and two x-ray detectors respectively associated therewith, the central rays of said x-ray sources intersecting in a common plane.

3. A lithotriptor as claimed in claim 2 wherein said central rays intersect in said common plane at an angle of approximately 90°.

4. A lithotriptor for disintegrating calculi in a patient comprising:
   a shockwave generator for generating shockwaves for disintegrating said calculi;

a drive means for driving said shockwave generator;

an x-ray system for generating an x-ray image of said calculus during disintegration thereof;

a detection circuit connected to an output of said x-ray system for generating a signal corresponding to the degree of disintegration of said calculus; and means connected to an output of said detection circuit and connected for controlling operation of said drive means for stopping said drive means and preventing further shockwaves from being generated when said signal from said detection circuit reaches a predetermined value.

5. A lithotriptor as claimed in claim 4 wherein said means connected to the output of said detection circuit includes a comparator.

6. A lithotriptor as claimed in claim 4 wherein said x-ray system comprises:

a first x-ray source having a first x-ray image intensifier associated therewith;

a second x-ray source having a second x-ray image intensifier associated therewith, said first and second x-ray sources having respective central rays intersecting in a common plane at said calculus;

and wherein said detection circuit comprises first and second detection circuit stages, said first detection circuit stage being connected to an output of said first x-ray image intensifier and said second detection circuit stage being connected to an output of said second x-ray image intensifier, each of said first and second detection circuit stages having an output connected to said means for controlling said drive means.

7. A method for operating a lithotriptor for disintegrating calculi in a patient by administering shockwaves to said calculi comprising the steps of:

applying shockwaves to said patient for disintegrating said calculi;

generating an x-ray image of said calculi during disintegration;

generating a signal from said x-ray image during disintegration corresponding to the degree of disintegration of said calculi; and using said signal corresponding to the degree of disintegration to automatically stop application of said shockwaves to said calculi when said signal reaches a predetermined value.

* * * * *